(12) United States Patent
Sasaki et al.

(10) Patent No.: US 10,159,872 B2
(45) Date of Patent: Dec. 25, 2018

(54) BALANCE TRAINING DEVICE AND BALANCE TRAINING METHOD

(71) Applicant: TOYOTA JIDOSHA KABUSHIKI KAISHA, Toyota-shi (JP)

(72) Inventors: Yu Sasaki, Toyota (JP); Masahiro Takahashi, Nagakute (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 0 days.

(21) Appl. No.: 15/263,085

(22) Filed: Sep. 12, 2016

(65) Prior Publication Data

US 2017/0072266 A1 Mar. 16, 2017

(30) Foreign Application Priority Data

Sep. 11, 2015 (JP) .................... 2015-180202

(51) Int. Cl.
*A63B 26/00* (2006.01)
*B62D 61/00* (2006.01)
(Continued)

(52) U.S. Cl.
CPC ............ *A63B 26/003* (2013.01); *A63B 22/16* (2013.01); *A63B 24/0087* (2013.01);
(Continued)

(58) Field of Classification Search
CPC ..... A61B 5/4023; A61B 5/486; A61B 26/003; A61B 2225/50; A61B 71/0622; A61B 2220/803
See application file for complete search history.

(56) References Cited

U.S. PATENT DOCUMENTS 5,052,406 A * 10/1991 Nashner ............... A61B 5/0488
600/595

FOREIGN PATENT DOCUMENTS

CN 1969741 A 5/2007
JP 2011-031669 A 2/2011
(Continued)

OTHER PUBLICATIONS

Office Action dated Oct. 9, 2018 in Chinese Patent Application No. 201610628649.7 with Machine English Translation.
(Continued)

*Primary Examiner* — Loan H Thanh
*Assistant Examiner* — Rae Fischer
(74) *Attorney, Agent, or Firm* — Oblon, McClelland, Maier & Neustadt, L.L.P.

(57) ABSTRACT

A balance training device includes an inverted two-wheel vehicle, a posture detection unit that detects a posture of the inverted two-wheel vehicle, a control unit that enables control of the inverted two-wheel vehicle so that the inverted two-wheel vehicle moves according to the posture of the inverted two-wheel vehicle detected by the posture detection unit and control of the inverted two-wheel vehicle so that the inverted two-wheel vehicle is forcibly moved in an arbitrary direction irrespective of the posture of the inverted two-wheel vehicle, and a position determining unit that determines a position of the inverted two-wheel vehicle. When a distance between the obtained position of the inverted two-wheel vehicle and the reference position is greater than or equal to a threshold, the control unit suppresses the control to forcibly move the inverted two-wheel vehicle in a direction from a reference position to the position of the inverted two-wheel vehicle.

7 Claims, 6 Drawing Sheets

(51) Int. Cl.
    *G05D 1/08*     (2006.01)
    *B62K 11/00*     (2006.01)
    *A63F 13/816*     (2014.01)
    *A63F 13/65*     (2014.01)
    *A63F 13/214*     (2014.01)
    *A63B 69/00*     (2006.01)
    *A63B 22/16*     (2006.01)
    *A63B 24/00*     (2006.01)
    *B62H 7/00*     (2006.01)
    *A63B 71/06*     (2006.01)
    *A61B 5/11*     (2006.01)
    *A61B 5/00*     (2006.01)

(52) U.S. Cl.
    CPC ........ A63B 69/0064 (2013.01); A63F 13/214 (2014.09); A63F 13/65 (2014.09); A63F 13/816 (2014.09); B62D 61/00 (2013.01); B62H 7/00 (2013.01); B62K 11/007 (2016.11); G05D 1/0891 (2013.01); *A61B 5/1116* (2013.01); *A61B 5/6887* (2013.01); *A61B 2505/09* (2013.01); *A63B 71/0622* (2013.01); *A63B 2024/009* (2013.01); *A63B 2024/0096* (2013.01); *A63B 2220/16* (2013.01); *A63B 2220/24* (2013.01); *A63B 2220/70* (2013.01); *A63B 2220/802* (2013.01); *A63B 2220/807* (2013.01); *A63B 2225/50* (2013.01)

(56) References Cited

FOREIGN PATENT DOCUMENTS

| | | |
|---|---|---|
| JP | 2011-203549 A | 10/2011 |
| JP | 2014-182318 A | 9/2014 |
| JP | 2014-184891 A | 10/2014 |
| JP | 2015-47962 A | 3/2015 |

OTHER PUBLICATIONS

Anna Parker, "Toyota launches a rehabilitation robot that can be customized for a training program", http://robot.ofweek.com/2014-06/ART-8321203-8220-28833439.html, Jun. 5, 2014.

\* cited by examiner

BALANCE TRAINING DEVICE AND BALANCE TRAINING METHOD

CROSS REFERENCE TO RELATED APPLICATION

This application is based upon and claims the benefit of priority from Japanese patent application No. 2015-180202, filed on Sep. 11, 2015, the disclosure of which is incorporated herein in its entirety by reference.

BACKGROUND

1. Field

The present disclosure relates to a balance training device and a balance training method, and in particular, to a technique for training an occupant's sense of balance using an inverted two-wheel vehicle that moves while maintaining an inverted state according to a change in an occupant's posture.

2. Description of Related Art

Japanese Unexamined Patent Application Publication No. 2011-31669 discloses a training system for an occupant riding on a coaxial two-wheel vehicle (an inverted two-wheel vehicle) to efficiently train occupant's physical function and balance function. This training system includes a coaxial two-wheel vehicle that travels while maintaining its inverted state according to a shift in an occupant's center of gravity. The coaxial two-wheel vehicle performs predetermined operations in back and forth and side to side directions in a fixed or random cycle. The occupant performs a travelling operation that moves his/her center of gravity back and forth or side to side according to the predetermined operations so that the coaxial two-wheel vehicle moves within a certain range. This improves the occupant's physical function, balance function, and the like in an enjoyable manner.

However, if there is a direction the occupant is not good at shifting his/her center of gravity in so as to restrict the inverted two-wheel vehicle's movement within a particular range, a position of the inverted two-wheel vehicle cannot be sufficiently returned to the direction in which the occupant is not good at shifting his/her center of gravity. That is, a direction opposite to the direction in which the occupant is not good at shifting the center of gravity is a challenge for the occupant to shift his/her center of gravity and is a direction in which the occupant finds it difficult to shift the center of gravity when the inverted two-wheel vehicle is forcibly moved in the direction. The present inventor has found a problem that the inverted two-wheel vehicle gradually moves in the direction the occupant is not good at shifting his/her center of gravity in, thus making it difficult to continue the training within the particular range of movement.

SUMMARY

The present disclosure provides a balance training device and a balance training method that enable training within a particular range of movement to be easily continued in training a sense of balance using an inverted two-wheel vehicle that moves while maintaining its inverted state according to a change in an occupant's posture.

A first exemplary aspect of the present disclosure is a balance training device including: an inverted two-wheel vehicle; a control unit that enables control of the inverted two-wheel vehicle so that the inverted two-wheel vehicle moves according to the posture of the inverted two-wheel vehicle detected by the posture detection unit and control of the inverted two-wheel vehicle so that the inverted two-wheel vehicle is forcibly moved in an arbitrary direction irrespective of the posture of the inverted two-wheel vehicle; and a position determining unit that determines a position of the inverted two-wheel vehicle. The balance training device is for balance training in which the occupant rides on the inverted two-wheel vehicle and training an occupant's sense of balance by operating the inverted two-wheel vehicle in such a way that the inverted two-wheel vehicle becomes closer to a predetermined reference position. When a distance between the position of the inverted two-wheel vehicle obtained by the position determining unit and the reference position is greater than or equal to a threshold, the control unit suppresses the control to forcibly move the inverted two-wheel vehicle in a direction from the reference position to the position of the inverted two-wheel vehicle.

In this way, when the inverted two-wheel vehicle moves to the direction the occupant is not good at shifting his/her center of gravity, it is possible to suppress the inverted two-wheel vehicle from moving further in the direction. That is, according to this exemplary aspect, it is possible to easily continue training within a particular range of movement.

In the above balance training device, the control unit may alternately switch between a normal mode in which the control unit controls the inverted two-wheel vehicle to move according to the posture of the inverted two-wheel vehicle detected by the posture detection unit and a challenge mode in which the control unit controls the inverted two-wheel vehicle to be forcibly moved in an arbitrary direction irrespective of the posture of the inverted two-wheel vehicle.

In the above balance training device, the control unit may calculate a time that is required for the occupant to return the inverted two-wheel vehicle from a position that is distant from the reference position by a predetermined distance to the reference position, and the control unit may reduce the threshold to become smaller as the calculated time becomes longer.

In this way, even a user who finds it difficult to return the inverted two-wheel vehicle to the reference position when the inverted two-wheel vehicle is at a great distance from the reference position can continue the balance training at a position close to the reference position. In the above balance training device, the control unit may operate at one of a plurality of levels and perform at least one of control to increase the number of times to switch from the normal mode to the challenge mode per unit of time as the level becomes higher and control to increase an amount of movement in the arbitrary direction as the level becomes higher, and the control unit may increase the threshold to be greater as the level becomes higher.

It is thus possible to adjust the threshold according to the level of the balance training in such a way that it will not easily fall in a state that requires suppression on providing challenges. Therefore, chances for training the sense of balance in the direction the trainee is not good at shifting his/her center of gravity as the challenges can be increased.

In the above balance training device, the control unit controls the inverted two-wheel vehicle so that the inverted two-wheel vehicle is moved in the arbitrary direction according to a control signal that is determined according to both of the posture of the inverted two-wheel vehicle and a parameter set independently from the posture of the inverted two-wheel vehicle to thereby control the inverted two-wheel vehicle to be forcibly moved in the arbitrary direction irrespective of the inverted two-wheel vehicle.

A second exemplary aspect of the present invention is a balance training method including a control step for executing control on an inverted two-wheel vehicle so that the inverted two-wheel vehicle moves according to a posture of the inverted two-wheel vehicle that changes according to a posture of an occupant riding on the inverted two-wheel vehicle and control on the inverted two-wheel vehicle so that the inverted two-wheel vehicle is forcibly moved in an arbitrary direction irrespective of the posture of the inverted two-wheel vehicle. The balance training method is for balance training in which the occupant rides on the inverted two-wheel vehicle and trains his/her sense of balance by operating the inverted two-wheel vehicle in such a way that the inverted two-wheel vehicle becomes closer to a predetermined reference position. In the control step, when a distance between a position of the inverted two-wheel vehicle and the reference position is greater than or equal to a threshold, the control to forcibly move the inverted two-wheel vehicle in a direction from the reference position to the position of the inverted two-wheel vehicle is suppressed.

According to the above exemplary aspects of the present invention, it is possible to provide a balance training device and a balance training method that enable training within a particular range of movement to be easily continued in training a sense of balance using an inverted two-wheel vehicle that moves while maintaining its inverted state according to a change in an occupant's posture.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE EXEMPLARY EMBODIMENTS

Hereinafter, a preferable exemplary embodiment of the present disclosure will be described with reference to the drawings. Specific numeric values indicated in the following exemplary embodiments are merely illustrative for easier understanding of the exemplary embodiment, and unless otherwise particularly specified, the present invention is not limited to them. Further, in the following descriptions and drawings, matters obvious to those skilled in the art are omitted and simplified as appropriate for clarity of the descriptions.

Exemplary Embodiment of the Invention

Figure 1:
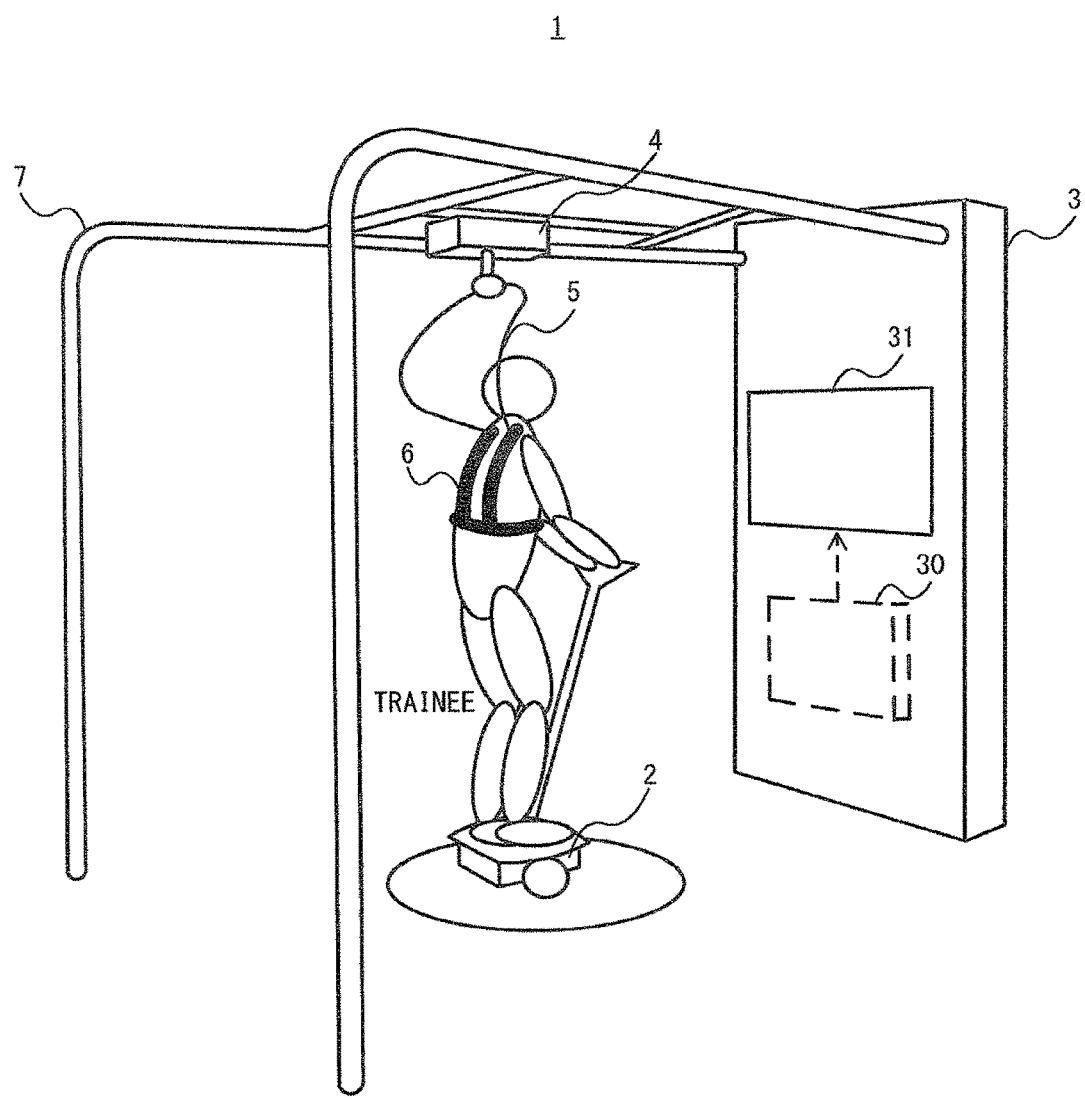
FIG. 1 is a structure diagram of a balance training device according to an exemplary embodiment.

A structure of a balance training device 1 according to an exemplary embodiment of the present invention will be described by referring to FIG. 1. As shown in FIG. 1, the balance training device 1 includes an inverted two-wheel vehicle 2, a training challenge providing device 3, a fixation member 4, a hanger 5, a belt 6, and a frame 7.

The inverted two-wheel vehicle 2 is a vehicle that a trainee (an occupant) is mounted on and moves. The inverted two-wheel vehicle 2 moves while maintaining its inverted state according to a change in a trainee's posture. The trainee refers to a training screen (a game screen) displayed on a display device 31 and moves the inverted two-wheel vehicle 2 to overcome challenges provided by the training challenge providing device 3 to thereby train a trainee's sense of balance. The intended trainees are, for example, a patient who has become hemiplegic after a stroke.

The training challenge providing device 3 provides challenges to the trainee. The training challenge providing device 3 includes a control device 30 and the display device 31.

The control device 30 is an information processing device that controls the balance training device 1. The control device 30 controls the inverted two-wheel vehicle 2 to execute an operation for providing the trainee with challenges in balance training that has been instructed by the trainee or a helper to be executed and also displays the training screen corresponding to the balance training on the display device 31.

The control device 30 includes a CPU (Central Processing Unit) and a storage unit and, by executing a program stored in the storage unit, executes processing as the control device 30 in this exemplary embodiment. That is, the program stored in the storage unit of the control device 30 includes codes for causing the CPU to execute the processing in the control device 30 according to this exemplary embodiment. Note that the storage unit is configured to include a storage device that can store, for example, this program and various information items used for the processing in the CPU. At least one arbitrary storage device such as a memory, a hard disk, and the like may be used as the storage device.

The control device 30 can communicate with a remote controller (not shown) that is operated by the trainee or the helper via radio communication. The control device 30 receives a radio signal transmitted from the remote controller in response to an input for instructing the execution of the balance training to the remote controller by the trainee or the helper. The radio signal indicates input contents for instructing the execution of the balance training.

The control device 30 starts executing the balance training in response to the radio signal. For example, the control device 30 controls the inverted two-wheel vehicle 2 to start an operation for the balance training. Further, the control device 30 starts displaying the training screen on the display device 31.

To be more specific, the control device 30 can communicate with the inverted two-wheel vehicle 2 via radio communication. The control device 30 transmits a radio signal for instructing the start of the balance training to the inverted two-wheel vehicle 2. In response to the radio signal, the inverted two-wheel vehicle 2 starts the operation for the balance training. The inverted two-wheel vehicle 2 transmits a radio signal indicating a position of the inverted two-wheel vehicle 2 that changes according to the execution of the balance training to the control device 30. The control device 30 reflects the position of the inverted two-wheel vehicle 2 indicated by the radio signal received from the inverted two-wheel vehicle 2 on the training screen displayed on the display device 31.

Figure 2:
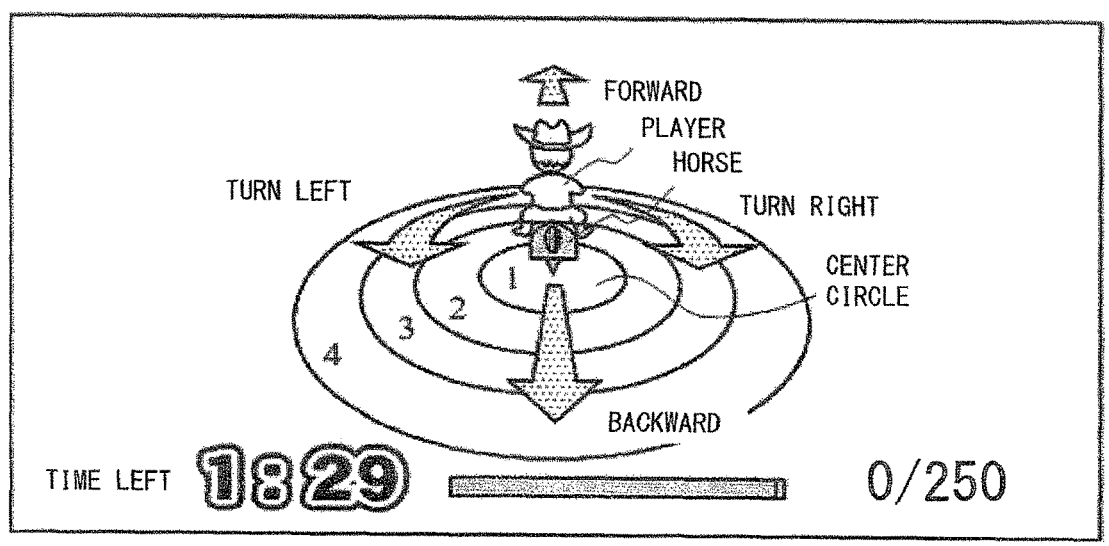
FIG. 2 is a drawing showing an example of a game screen of a rodeo game according to the exemplary embodiment.

An example of the training screen will be described by referring to FIG. 2. FIG. 2 shows an example in which contents of the balance training (game contents) are a rodeo game. On the training screen, the inverted two-wheel vehicle 2 and the trainee are drawn as a horse and a player riding on the horse, respectively. On the training screen, a plurality of circles having radii different from each other is drawn with respect to a predetermined reference position at the center of the circles.

While the rodeo game is being executed, the inverted two-wheel vehicle 2 intermittently moves at random irrespective of operations of the trainee. The trainee changes his/her posture so that the inverted two-wheel vehicle 2 is positioned at the reference position while the inverted two-wheel vehicle 2 moves as described above to thereby train the trainee's sense of balance. At this time, the control device 30 moves the horse to positions corresponding to the positions of the inverted two-wheel vehicle 2 and displays the horse on the training screen. The rodeo game is executed for a predetermined time, and in the predetermined time, the smaller the circle the horse is located at, the higher the score will be.

As described above, the training screen is displayed on the display device 31 by the control device 30. The display device 31 is, for example, a liquid crystal display, an organic EL display, a plasma display, or the like.

The fixation member 4 is fixed to an upper frame member of the frame 7 at a position higher than the inverted two-wheel vehicle 2 and the occupant riding on the inverted two-wheel vehicle 2. The hanger 5 is connected to the fixation member 4 and the occupant. The hanger 5 is a string-like member containing a stretchable material that contains an elastic material such as rubber, springs, or the like. The hanger 5 is connected to the occupant by the belt 8. The belt 8 is worn on an upper body of the occupant.

With such a structure, the hanger 5 supports the occupant by pulling the occupant upward. This enables the occupant to easily maintain his/her standing posture even when the occupant is displaced from the inverted two-wheel vehicle 2, thereby improving safety.

Figure 3:
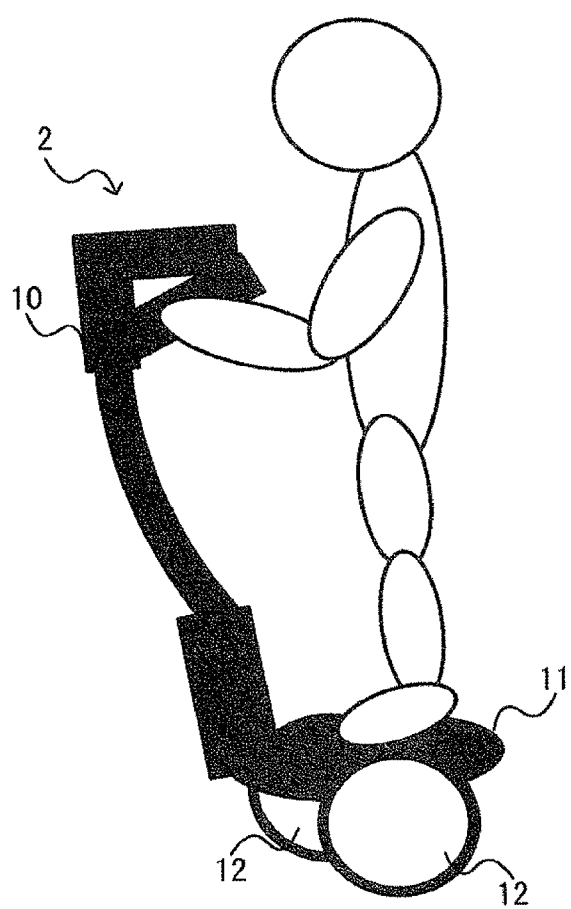
FIG. 3 is an external structure diagram of an inverted two-wheel vehicle according to the exemplary embodiment.

Next, an external structure of the inverted two-wheel vehicle 2 according to the exemplary embodiment of the present disclosure will be described by referring to FIG. 3. As shown in FIG. 3, the inverted two-wheel vehicle 2 includes a handlebar 10, a step cover 11, and a pair of right and left wheels 12.

The inverted two-wheel vehicle 2 rotates the right and left wheels 12 to maintain the inverted state of the inverted two-wheel vehicle 2 according to changes in the occupant's posture in the back and forth direction of the inverted two-wheel vehicle 2 that are generated when the trainee who is holding the handlebar 10 and mounted on the step cover 11 exerts a load on the inverted two-wheel vehicle 2 in the back and forth direction thereof. That is, when the trainee tilts a posture of the inverted two-wheel vehicle 2 forward, the inverted two-wheel vehicle 2 travels forward to maintain its inverted state, while when the trainee tilts the posture of the inverted two-wheel vehicle 2 backward, the inverted two-wheel vehicle 2 rotates the right and left wheels 12 so that the inverted two-wheel vehicle 2 travels backward to maintain its inverted state.

Moreover, the inverted two-wheel vehicle 2 rotates the right and left wheels 12 so that the inverted two wheel vehicle 2 performs a turn operation according to a change in a posture of the inverted two-wheel vehicle 2 in the right and left direction generated when the trainee who is holding the handlebar 10 and mounted on the step cover 11 exerts a load on the inverted two-wheel vehicle 2 in the right and left direction thereof. That is, the inverted two-wheel vehicle rotates the right and left wheels 12 so that when the trainee tilts the posture of the inverted two-wheel vehicle 2 to the left, the inverted two-wheel vehicle 2 turns the inverted two-wheel vehicle 2 counterclockwise, while when the trainee tilts the posture of the inverted two-wheel vehicle 2 to the right, the inverted two-wheel vehicle 2 turns the inverted two-wheel vehicle 2 clockwise.

The handlebar 10 is attached in front of the step cover 11 of the inverted two-wheel vehicle 2 and extends upward so that the trainee who is mounted on the step cover 11 can hold the handlebar 10 by both hands. The trainee tilts the handlebar 10 in the right and left direction according to the load exerted on the inverted two-wheel vehicle 2 in the right and left direction.

The step cover 11 is a loading part on which both of the occupant's feet can be mounted. The step cover 11 is tilted in the back and forth direction together with the whole inverted two-wheel vehicle 2 according to the load exerted by the occupant on the inverted two-wheel vehicle 2 in the back and forth direction thereof. Further, the step cover 11 is tilted in the right and left direction together with the handlebar 10 according to the load exerted by the occupant on the inverted two-wheel vehicle 2 in the right and left direction thereof. More specifically, the inverted two-wheel vehicle 2 has a link mechanism including the handlebar 10 and the step cover 11. Then, when the occupant shifts the load on his/her right foot and tilts his/her posture to the left, the step cover 11 is tilted to the left by the link mechanism, and the handlebar 10 is tilted to the left as it is linked with the step cover 11. When the occupant shifts the load on his/her left foot and tilts his/her posture to the right, the step cover 11 is tilted to the right by the link mechanism, and the handlebar 10 is tilted to the right as it is linked of the step cover 11. The link mechanism functions as an operation unit for turning the inverted two-wheel vehicle 2. Note that the handlebar 10 may not be coupled to the link mechanism including the step cover 11 and may instead be independently provided.

The wheels 12 are provided below the step cover 11 of the inverted two-wheel vehicle 2. There are two of the wheels 12 so that they are symmetric in the inverted two-wheel vehicle 2.

Figure 4:
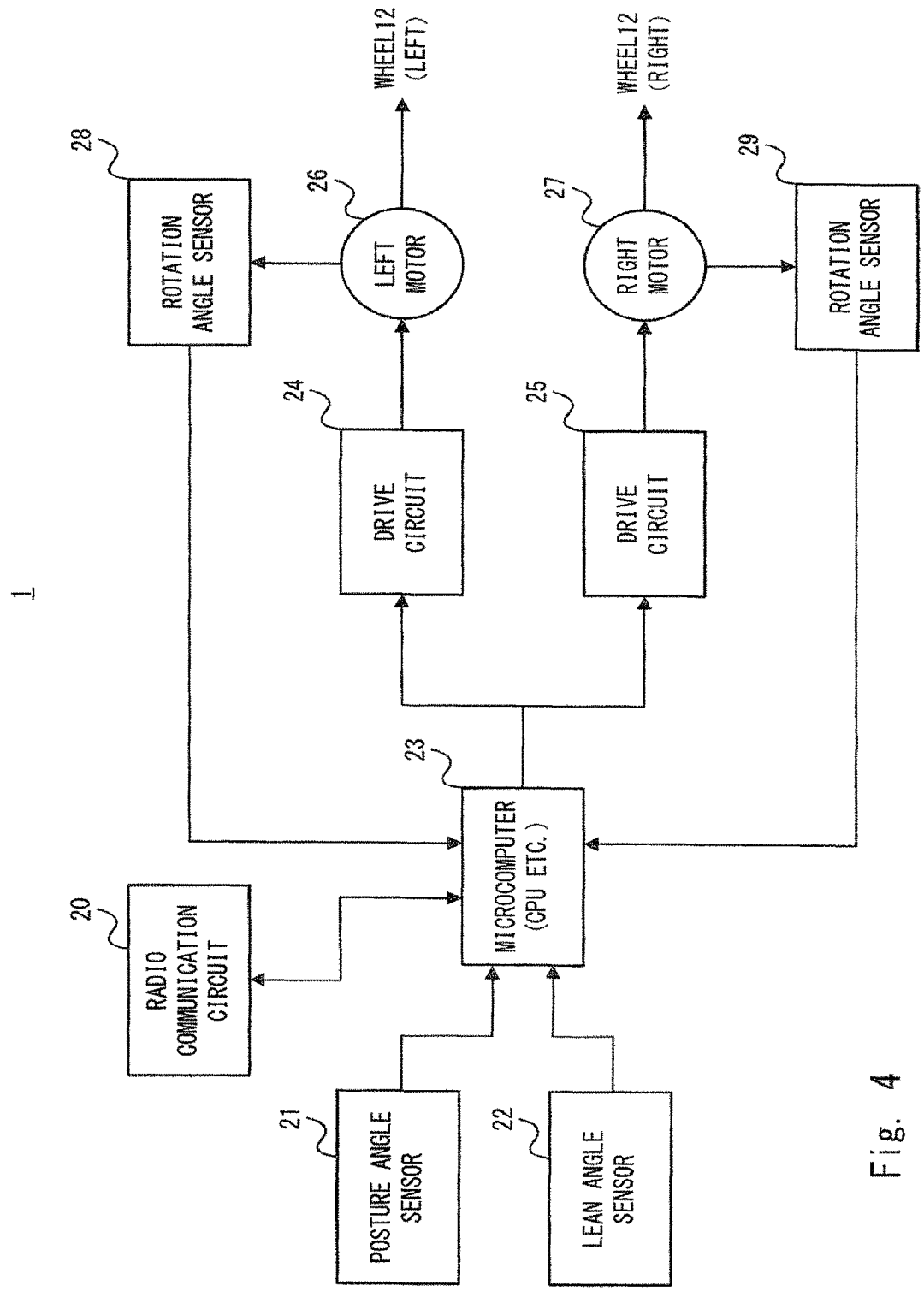
FIG. 4 is an internal configuration diagram of the inverted two-wheel vehicle according to the exemplary embodiment.

Next, an internal configuration of the inverted two-wheel vehicle 2 according to the exemplary embodiment of the present invention will be described with reference to FIG. 4. As shown in FIG. 4, the inverted two-wheel vehicle 2 includes a radio communication circuit 20, a posture angle sensor 21, a lean angle sensor 22, a microcontroller 23, drive circuits 24 and 25, motors 26 and 27, and rotation angle sensors 28 and 29.

The radio communication circuit 20 transmits and receives arbitrary information using radio signals with the control device 30. The radio communication circuit 20 converts information output from the microcomputer 23 from electric signals into radio signals and transmits the radio signals to the control device 30. The radio communication circuit 20 converts information received from the control device 30 from radio signals into electric signals and outputs the electric signals to the microcomputer 23. Note that any radio communication standard can be employed for these radio signals.

The posture angle sensor 21 detects a posture angle of the inverted two-wheel vehicle 2 in the back and forth direction (an angle around a pitch axis) that changes when the trainee exerts the load on the step cover 11 in the back and forth direction of the inverted two-wheel vehicle 2. The posture angle sensor 21 generates a posture angle signal indicating the detected posture angle and outputs the posture angle signal to the microcomputer 23. Hereinafter, the angle around the pitch axis of the inverted two-wheel vehicle 2 will also be referred to as a "pitch angle".

The lean angle sensor 22 detects a tilt angle of the step cover 11 in the right and left direction (an angle around a roll axis) as a lean angle, generates a lean angle signal indicating the lean angle, and outputs the lean angle signal to the microcomputer 23. Note that as described above, as the step cover 11 and the handlebar 10 are linked by the link mechanism, the tilt angle detected by the lean angle sensor 22 corresponds to a tilt angle of the handlebar 10 in the right and left direction thereof. Both of the posture angle detected by the posture angle sensor 21 and the lean angle detected by the lean angle sensor 22 may be referred to herein as "posture angle."

As described above, the microcomputer 23 is an ECU (Electronic Control Unit) that controls the motors 26 and 27 to maintain the inverted state of the inverted two-wheel vehicle 2. The microcomputer 23 includes a CPU and a storage unit and executes processing as the microcomputer 23 according to this exemplary embodiment by executing a program stored in the storage unit. That is, the program stored in the storage unit of the microcomputer 23 includes codes for causing the CPU to execute the processing in the microcomputer 23 according to the exemplary embodiment. Note that the storage unit is configured to include a storage device that can store, for example, this program and various information items used for the processing by the CPU. At least one arbitrary storage device such as a memory, a hard disk, and the like may be used as the storage device.

The microcomputer 23 outputs command values for controlling the motor 26 to the drive circuit 24. Further, the microcomputer 23 outputs command values for controlling the motor 27 to the drive circuit 25. More specifically, the microcomputer 23 generates the command values for controlling the motors 26 and 27 to maintain the inverted state of the inverted two-wheel vehicle 2 according to the posture angle of the inverted two-wheel vehicle 2 indicated by the posture angle signal output from the posture angle sensor 21.

The microcomputer 23 generates the command values so that the inverted two-wheel vehicle 2 travels forward when the posture angle is an angle that tilts forward more than a predetermined reference posture angle. On the other hand, the microcomputer 23 generates the command values so that the inverted two-wheel vehicle 2 travels backward when the posture angle is an angle that tilts backward more than the predetermined reference posture angle. Note that as a difference between the above reference posture angle and the posture angle becomes greater, the microcomputer 23 generates the command values so that the inverted two-wheel vehicle 2 is accelerated more.

The microcomputer 23 generates the command values for controlling the motors 26 and 27 so that the inverted two-wheel vehicle 2 turns according to the lean angle of the inverted two-wheel vehicle 2 indicated by the lean angle signal output from the lean angle sensor 22.

When the lean angle tilts to the right with respect to a predetermined reference tilt angle of the inverted two-wheel vehicle 2, the microcomputer 23 generates the command values so that the inverted two-wheel vehicle 2 travels to the right. On the other hand, when the lean angle tilts to the left with respect to the predetermined reference tilt angle of the inverted two-wheel vehicle 2, the microcomputer 23 generates the command values so that the inverted two-wheel vehicle 2 travels to the left. Note that as a difference between the above reference tilt angle and the lean angle becomes greater, the microcomputer 23 generates the command values so that the inverted two-wheel vehicle 2 turns more sharply (so that a turn radius of the inverted two-wheel vehicle 2 will become smaller).

The drive circuit 24 generates a drive current for driving the motor 26 according to the command values output from the microcomputer 23 and supplies the drive current to the motor 26. The drive circuit 25 generates a drive current for driving the motor 27 according to the command values output from the microcomputer 23 and supplies the drive current to the motor 27.

The motor 26 is driven by the drive current supplied from the drive circuit 24. By driving the motor 26, the left wheel 12 of the inverted two-wheel vehicle 2 rotates. The motor 27 is driven by the drive current supplied from the drive circuit 25. By driving the motor 27, the right wheel 12 of the inverted two-wheel vehicle 2 rotates.

The rotation angle sensor 28 detects a rotation angle of the motor 26, generates a rotation angle signal indicating the detected rotation angle, and outputs the rotation angle signal to the microcomputer 23. The rotation angle sensor 29 detects a rotation angle of the motor 27, generates a rotation angle signal indicating the detected rotation angle, and outputs the rotation angle signal to the microcomputer 23.

In this exemplary embodiment, the microcomputer 23 alternately switches between a normal mode and a challenge mode to execute the above operation for the balance training. In other words, the microcomputer 23 includes the normal mode and the challenge mode as operation modes.

In the normal mode, the microcomputer 23 controls the inverted two-wheel vehicle 2 so that the inverted two-wheel vehicle 2 moves while maintaining its inverted state according to the posture of the inverted two-wheel vehicle 2. That is, in the normal mode, as described above, the microcomputer 23 controls the inverted two-wheel vehicle 2 according to the posture angle indicated by the posture angle signal from the posture angle sensor 21 and the lean angle indicated by the lean angle signal from the lean angle sensor 22.

On the other hand, in the challenge mode, the microcomputer 23 controls the inverted two-wheel vehicle 2 so that the inverted two-wheel vehicle forcibly moves in an arbitrary direction independent of the posture of the inverted two-wheel vehicle 2. The microcomputer 23 changes at least one of the posture angle indicated by the posture angle signal from the posture angle sensor 21 and the lean angle indicated by the lean angle signal from the lean angle sensor 22 by adding an offset value(s) (a parameter(s) specified independently from the posture of the inverted two-wheel vehicle 2) generated by a random number and controls the inverted two-wheel vehicle 2 according to (a control signal indicating) the changed posture angle and/or the changed lean angle. Note that the offset value is not limited to a value generated by a random number and may instead be values of a predetermined pattern.

Moreover, when either one of the posture angle and the lean angle is changed, the angle to be changed can be determined at random or determined in a predetermined order. When both the posture angle and the lean angle are changed, the offset value added to the posture angle may be the same as that added to the lean angle or an offset value added to the posture angle may be different from that added to the lean angle.

As described above, the microcomputer 23 intermittently executes switching from the normal mode to the challenge mode and switching from the challenge mode to the normal mode in an alternate manner to thereby randomly move the inverted two-wheel vehicle 2 irrespective of the operations of the trainee as the challenges in the rodeo game. The above switching of the operation modes may be performed at a fixed time interval or at a random time interval.

Further, the microcomputer 23 uses a position of the inverted two-wheel vehicle 2 when the balance training has started as a reference position and calculates a position of the inverted two-wheel vehicle 2 during the balance training as needed according to the rotation angle of the motor 26 indicated by the rotation angle signal output from the rotation angle sensor 28 and the rotation angle of the motor 27 indicated by the rotation angle signal output from the rotation angle sensor 29. Any commonly conceivable method may be used as a method of calculating the position of the inverted two-wheel vehicle 2 during the balance training. For example, the microcomputer 23 may calculate the position of the inverted two-wheel vehicle 2 during the balance training according to radii of the wheels 12 and values of the rotation angles of the motors 26 and 27 accumulated since the balance training started.

Then, the microcomputer 23 transmits information indicating the calculated position of the inverted two-wheel vehicle 2 to the control device 30 via the radio communication circuit 20. As described above, the control device 30 displays the position of the inverted two-wheel vehicle 2 on the training screen according to the information received from the inverted two-wheel vehicle 2.

Further, the microcomputer 23 uses the position of the inverted two-wheel vehicle 2 during the balance training that has been calculated in this way for suppression to prevent the challenges from being provided in the direction the trainee is not good at shifting his/her center of gravity in, which will be described later. That is, when the position of the inverted two-wheel vehicle 2 during the balance training is at a great distance from the reference position, the direction at which the inverted two-wheel vehicle 2 is positioned from the reference position is a direction in which the trainee is not good at shifting his/her center of gravity when the inverted two-wheel vehicle 2 is forcibly moved as the challenges. Accordingly, the microcomputer 23 prevents the forced movement of the inverted two-wheel vehicle in the direction the trainee is not good at shifting this/her center of gravity in. This enables the balance training to be continued within a particular range of movement.

Figure 5:
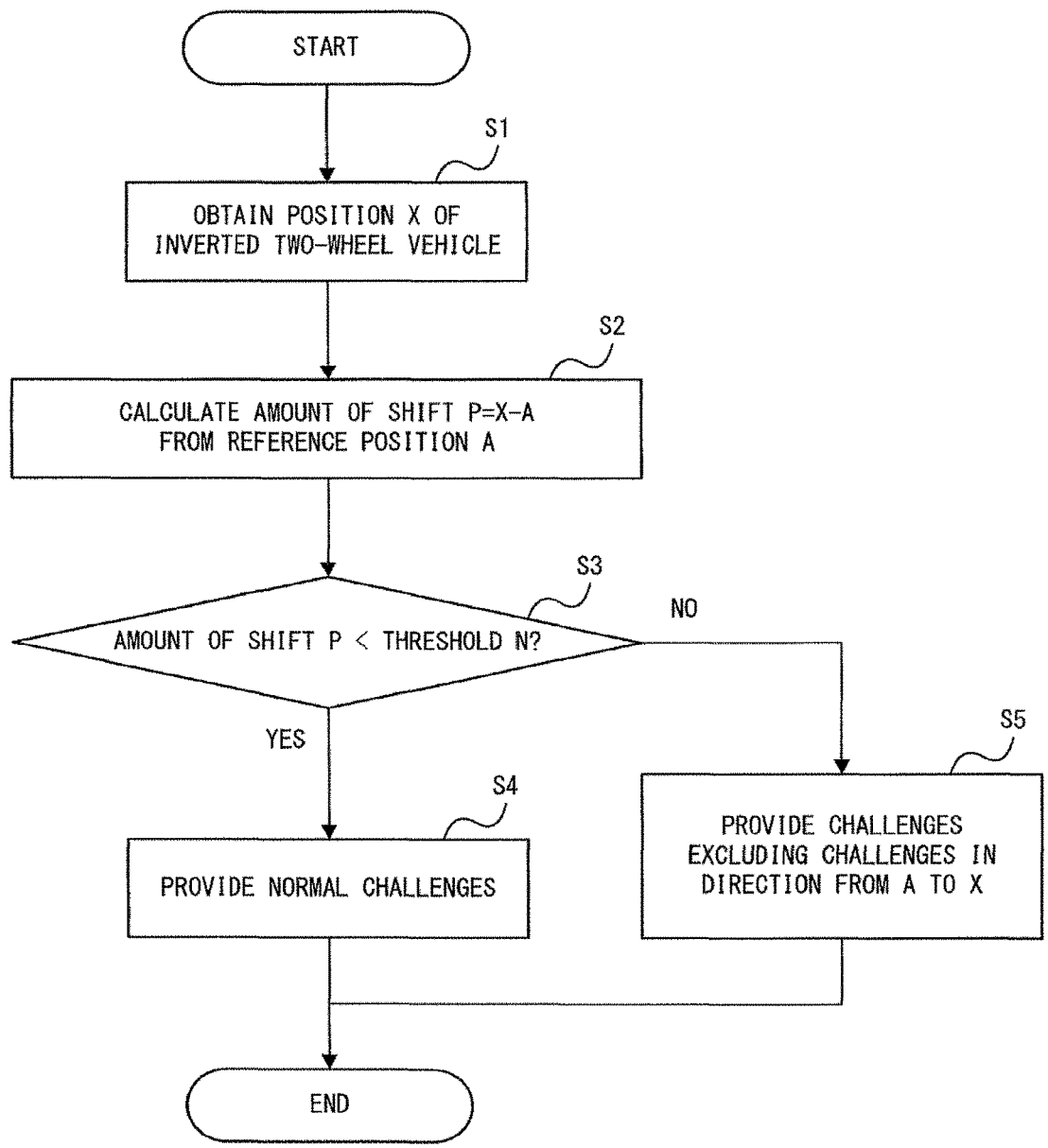
FIG. 5 is a flowchart showing an operation of the balance training device according to the exemplary embodiment.
Figure 6:
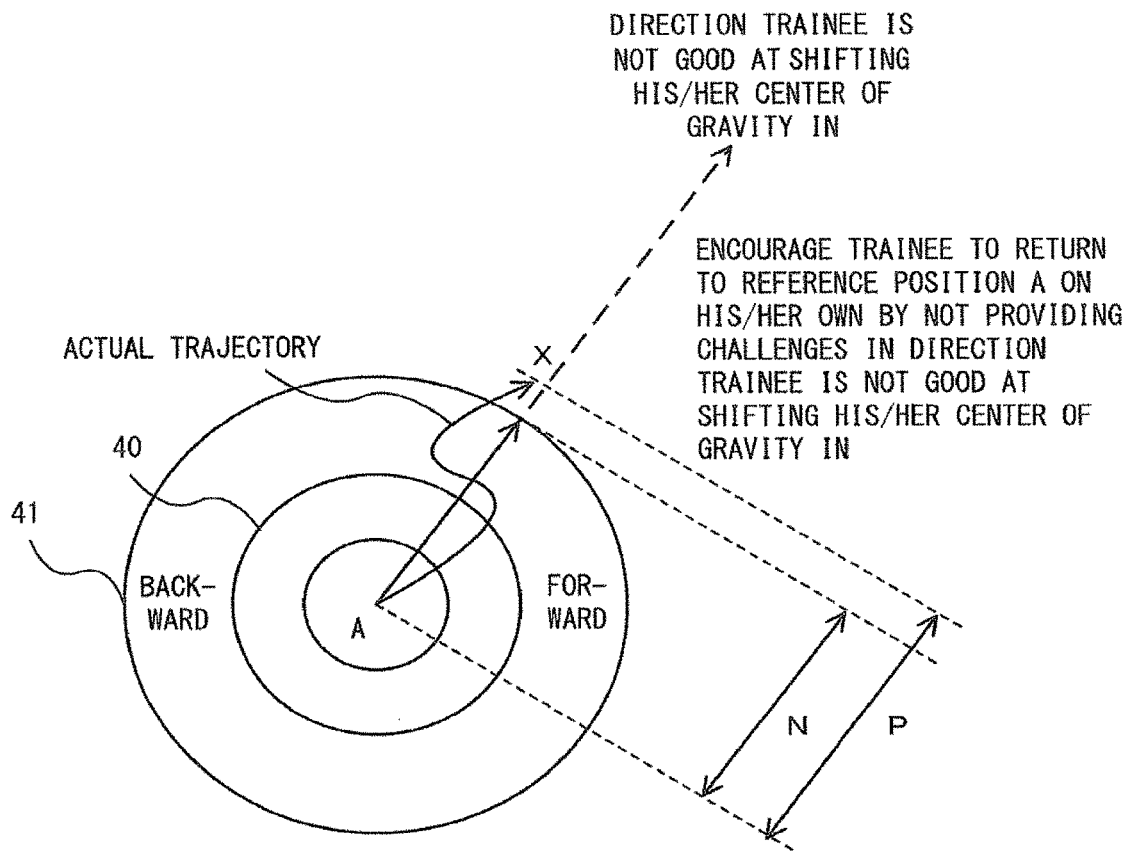
FIG. 6 is a drawing showing an example of movement of the inverted two-wheel vehicle according to the exemplary embodiment.

Next, an operation of the balance training device 1 according to the exemplary embodiment of the present invention will be described by referring to FIGS. 5 and 6. While the challenge mode is being executed, the microcomputer 23 repeats the process shown in FIG. 5 to prevent the challenges being provided in the direction which the trainee is not good at shifting his/her center of gravity in, and thus enabling the balance training to be continued within a particular range of movement. Note that in FIG. 6, a circle 40 centered at the reference position indicates an outermost peripheral circle in which scores can be added in the rodeo game, and a circle 41 with a greater radius than that of the circle 40 centered at the reference position is a reference for evaluating as to whether or not the challenges should be prevented from being provided in the direction the trainee is not good at shifting his/her center of gravity in.

The microcomputer 23 determines a position X of the inverted two-wheel vehicle 2 (S1). To be more specific, the microcomputer 23 calculates the current position X of the inverted two-wheel vehicle 2 with respect to a reference position A according to the rotation angle of the motor 26 indicated by the rotation angle signal output from the rotation angle sensor 28 and the rotation angle of the motor 27 indicated by the rotation angle signal output from the rotation angle sensor 29.

The microcomputer 23 calculates an amount of shift P of the calculated current position X of the inverted two-wheel vehicle 2 from the reference position A (S2). In other words, the microcomputer 23 calculates a distance P between the reference position A and the current position X of the inverted two-wheel vehicle 2.

The microcomputer 23 evaluates as to whether or not the calculated amount of shift P is smaller than a predetermined threshold N (S3). When the amount of shift P is smaller than the threshold N (S3: Yes), the microcomputer 23 provides normal challenges (S4). That is, the microcomputer 23 changes at least one of the posture angle indicated by the posture angle signal from the posture angle sensor 21 and the lean angle indicated by the lean angle signal from the lean angle sensor 22 by adding an offset value(s) generated using a random number(s), and controls the inverted two-wheel vehicle 2 according to the changed posture angle and/or the changed lean angle.

On the other hand, when the amount of shift P is greater than or equal to the threshold N (S3: No), the microcomputer 23 provides challenges except for the challenges in the direction from the reference position A to the current position X of the inverted two-wheel vehicle 2 (the direction the trainee is not good at shifting his/her center of gravity in) (S5). That is, the microcomputer 23 prevents forced movement of the inverted two-wheel vehicle 2 in the direction from the reference position A to the current position X of the inverted two-wheel vehicle 2 as the challenges.

For example, when the direction from the reference position A to the current position X of the inverted two-wheel vehicle 2 is a forward direction of the inverted two-wheel vehicle 2, the microcomputer 23 excludes movement in the forward direction of the inverted two-wheel vehicle 2 from the directions to forcibly move the inverted two-wheel vehicle 2 as the challenges. To be more specific, the microcomputer 23 excludes application of an offset value that changes the posture angle to tilt forward and applies only an offset value that changes the posture angle to tilt backward.

For example, when the direction from the reference position A to the current position X of the inverted two-wheel vehicle 2 is a backward direction of the inverted two-wheel vehicle 2, the microcomputer 23 excludes movement in the backward direction of the inverted two-wheel vehicle 2 from the directions to forcibly move the inverted two-wheel vehicle 2 as the challenges. To be more specific, the microcomputer 23 excludes application of an offset value that changes the posture angle to tilt backward and applies only an offset value that changes the posture angle to tilt forward.

For example, when the direction from the reference position A to the current position X of the inverted two-wheel vehicle 2 is a right direction of the inverted two-wheel vehicle 2, the microcomputer 23 excludes movement in the right direction of the inverted two-wheel vehicle 2 from the directions to forcibly move the inverted two-wheel vehicle 2 as the challenges. To be more specific, the microcomputer 23 excludes application of an offset value that changes the posture angle to tilt to the right and applies only an offset value that changes the posture angle to tilt to the left.

For example, when the direction from the reference position A to the current position X of the inverted two-wheel vehicle 2 is a left direction of the inverted two-wheel vehicle 2, the microcomputer 23 excludes movement in the left direction of the inverted two-wheel vehicle 2 from the directions to forcibly move the inverted two-wheel vehicle 2 as the challenges. To be more specific, the microcomputer 23 excludes application of an offset value that changes the posture angle to tilt to the left and applies only an offset value that changes the posture angle to tilt to the right.

When the direction from the reference position A to the current position X of the inverted two-wheel vehicle 2 is an oblique direction with respect to the back and forth, and right and left directions of the inverted two-wheel vehicle 2, a vector of the direction from the reference position A to the current position X of the inverted two-wheel vehicle 2 may be divided into a component of the back and forth direction and a component of the right and right direction. Then, the direction of the vector having the greater component may be excluded from the directions in which the inverted two-wheel vehicle 2 is forcibly moved as the challenges.

Further, it is not limited to prevent (completely exclude) the challenges from being provided in the direction from the reference position A to the current position X of the inverted two-wheel vehicle 2, and it may be possible to suppress (reduce the degree of) providing the challenges in the direction. The suppression here includes prevention. For example, the microcomputer 23 may reduce an amount of forced movement of the inverted two-wheel vehicle 2 in the direction from the reference position A to the current position X of the inverted two-wheel vehicle as the challenges so that it will be smaller than an amount of forced movement of the inverted two-wheel vehicle 2 in the other directions. As another example, the microcomputer 23 may reduce the offset value to be added to the posture angle or the lean angle by a predetermined ratio in the direction from the reference position A to the current position X of the inverted two-wheel vehicle 2 as compared to that in the other directions.

Alternatively, as the suppression on providing the challenges in the direction from the reference position A to the current position X of the inverted position X, the microcomputer 23 may reduce a frequency in which the inverted two-wheel vehicle 2 is forcibly moved in the corresponding direction as the challenges so that it will be lower than a frequency in which the inverted two-wheel vehicle 2 is forcibly moved in other directions.

When the direction from the reference position A to the current position X of the inverted two-wheel vehicle 2 is an oblique direction with respect to the back and forth and right and left directions of the inverted two-wheel vehicle 2, a vector of the direction from the reference position A to the current position X of the inverted two-wheel vehicle 2 may be divided into a component of the back and forth direction and a component of the right and right direction. Then, it may be possible to suppress providing the challenges in the direction of the vector having a greater component between the divided components.

Alternatively, it may be possible to suppress providing the challenges in the directions of the vectors of the divided components. In this case, in regard to the degree of suppressing providing the challenges in the directions of the vectors of the divided components, the greater the vectors of the divided components, the more the degree of suppressing providing the challenges can be increased. For example, as the vector becomes greater, the ratio to reduce the offset value may be increased. Alternatively, for example, as the vector becomes greater, the frequency in which the inverted two-wheel vehicle 2 is forcibly moved may be reduced.

As described above, the balance training device 1 according to this exemplary embodiment includes an inverted two-wheel vehicle 2, a posture detection unit (corresponding to the posture angle sensor 21 and the lean angle sensor 22) that detects the posture of the inverted two-wheel vehicle 2 that changes according to the posture of the occupant who rides on the inverted two-wheel vehicle 2, and a control unit (corresponding to the microcomputer 23) that enables control on the inverted two-wheel vehicle so that the inverted two-wheel vehicle 2 moves according to the posture of the inverted two-wheel vehicle 2 detected by the posture detection unit and control on the inverted two-wheel vehicle 2 so that the inverted two-wheel vehicle 2 is forcibly moved in an arbitrary direction irrespective of the posture of the inverted two-wheel vehicle 2. The balance training device 1 is for the balance training in which the occupant rides on the inverted two-wheel vehicle 2 and trains the trainee's sense of balance by operating the inverted two-wheel vehicle 2 so that it will be closer to a predetermined reference position. The balance training device 1 further includes a position determining unit (corresponding to the microcomputer 23) that determines the position of the inverted two-wheel vehicle 2. When the distance between the position of the inverted two-wheel vehicle 2 obtained by the position determining unit and the reference position is greater than or equal to a threshold, the control unit suppresses the control to forcibly move the inverted two-wheel vehicle 2 in the direction in which the inverted two-wheel vehicle 2 is positioned from the reference position.

Thus, when the inverted two-wheel vehicle 2 moves in the direction the occupant is not good at shifting his/her center of gravity in, it is possible to suppress the inverted two-wheel vehicle 2 from moving further in the direction. That is, according to this exemplary embodiment, it is possible to easily continue training within a particular range of movement.

Other Exemplary Embodiments

Although an example in which the threshold N is a predetermined fixed value has been explained in the above exemplary embodiment, it is not limited to this. The threshold N may be variable. For example, the microcomputer 23 measures a time from when the distance between the reference position A and the position X of the inverted two-wheel vehicle 2 becomes a predetermined distance until the position X of the inverted two-wheel vehicle 2 returns to the reference position A. Then, the microcomputer 23 may change the threshold N according to the measured time. For example, the microcomputer 23 changes the threshold N to be smaller as the measured time becomes longer.

In this way, even a user who finds it difficult to return the inverted two-wheel vehicle 2 to the reference position when the inverted two-wheel vehicle 2 is at a great distance from the reference position, can continue the balance training at a position closer to the reference position. This enables, for example, the user to easily get high scores in the rodeo game and thus motivate the user to continue training in the rodeo game.

Additionally, in the above exemplary embodiment, the inverted two-wheel vehicle 2 may have a plurality of levels in the operation for the balance training. That is, the higher the level, the more difficult the balance training will be. These levels can be specified by the trainee or the helper using the remote controller when the trainee or the helper instructs the execution of the balance training. That is, the control device 30 receives a radio signal transmitted from the remote controller in response to an input that selects the level of the balance training and instructs the execution of the balance training on the remote controller from the trainee or the helper. The radio signal selects the level of the balance training and indicates input contents for instructing the execution of the balance training.

The control device 30 controls the execution of the balance training at the selected level according to the radio signal. For example, the control device 30 transmits the radio signal that instructs a start of the balance training at the selected level to the inverted two-wheel vehicle 2. In response to the radio signal received via the radio communication circuit 20, the microcomputer 23 of the inverted two-wheel vehicle 2 starts the operation for the balance training at the selected level instructed by the radio signal.

The microcomputer 23 performs at least one of control that increases the number of times to switch from the normal mode to the challenge mode per unit of time as the selected level becomes higher and control that increases the amount of movement in an arbitrary direction as the selected level becomes higher. That is, as the selected level becomes higher, the microcomputer 23 controls a time from when the operation mode is switched to the normal mode until the operation mode is switched again to the challenge mode to become shorter. Moreover, as the selected level becomes higher, the microcomputer 23 increases the above offset value. That is, as the selected level increases, the microcomputer 23 changes the threshold N to be greater.

It is thus possible to adjust the threshold according to the level of the balance training in such a way that it will not easily fall into a state requiring that providing of the challenges be suppressed. Therefore, chances of training the trainee's sense of balance in the direction he/she is not good at shifting his/her center of gravity in as the challenges can be increased.

Note that the present invention is not limited to the above-described exemplary embodiments, and modifications can be made as appropriate without departing from the scope thereof.

Note that in the above exemplary embodiment, although an example is given in which the microcomputer 23 determines the position of the inverted two-wheel vehicle 2 by the microcomputer 23 calculating the position of the inverted two-wheel vehicle 2 according to the rotation angles of the motors 26 and 27 indicated by the rotation angle signal output from the rotation angle sensors 28 and 29, it is not limited to this. The balance training device 1 may include, for example, a sensor (a camera, an infrared sensor, an ultrasonic sensor, or the like) that observes the position of the inverted two-wheel vehicle 2 from outside the inverted two-wheel vehicle 2 and may obtain the position of the inverted two-wheel vehicle 2 according to a result of the observation of the sensor.

Such a sensor is mounted on, for example, the frame 7 in order to observe the position of the inverted two-wheel vehicle 2 from above the inverted two-wheel vehicle 2. The control device 30 receives sensor data generated by the sensor and calculates the position of the inverted two-wheel vehicle 2 according to the received sensor data. The control device 30 transmits information indicating the calculated position of the inverted two-wheel vehicle by radio communication to the inverted two-wheel vehicle 2. Then, the microcomputer 23 of the inverted two-wheel vehicle 2 may receive the information transmitted from the control device 30 via the radio communication circuit 20 and obtain the position of the inverted two-wheel vehicle 2 indicated by the received information.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A balance training device comprising:
an inverted vehicle;
a posture detection unit that detects a posture of the inverted vehicle, the posture changing according to a posture of an occupant riding on the inverted vehicle;
a control unit that controls the inverted vehicle so that the inverted vehicle moves within a predetermined range according to the posture of the inverted vehicle detected by the posture detection unit and controls the inverted vehicle so that the inverted vehicle is forcibly moved in an arbitrary direction irrespective of the posture of the inverted vehicle; and
a position determining unit that determines a position of the inverted vehicle, wherein
when a distance between the position of the inverted vehicle obtained by the position determining unit and a reference position is greater than or equal to a threshold, the control unit suppresses only the control to forcibly move the inverted vehicle in a direction from the reference position to the position of the inverted vehicle when the control unit controls the inverted vehicle so that the inverted vehicle is forcibly moved in an arbitrary direction irrespective of the posture of the inverted vehicle.

2. The balance training device according to claim 1, wherein the control unit alternately switches between a normal mode in which the control unit controls the inverted vehicle to move within the predetermined range according to the posture of the inverted vehicle detected by the posture detection unit and a challenge mode in which the control unit controls the inverted vehicle to be forcibly moved in an arbitrary direction irrespective of the posture of the inverted vehicle.

3. The balance training device according to claim 2, wherein the control unit calculates a time that is required for the occupant to return the inverted vehicle from a position that is distant from the reference position by a predetermined distance to the reference position, and the control unit reduces the threshold to become smaller as the calculated time becomes longer.

4. The balance training device according to claim 2, wherein
the control unit operates at one of a plurality of levels and performs at least one of control to increase the number of times to switch from the normal mode to the challenge mode per unit of time as the level becomes higher and control to increase an amount of movement in the arbitrary direction as the level becomes higher, and
the control unit increases the threshold to be greater as the level becomes higher.

5. An inverted vehicle, comprising:
a posture detection unit that detects a posture of the inverted vehicle, the posture changing according to a posture of an occupant riding on the inverted vehicle;
a control unit that controls the inverted vehicle so that the inverted vehicle moves within a predetermined range according to the posture of the inverted vehicle detected by the posture detection unit and controls the inverted vehicle so that the inverted vehicle is forcibly moved in an arbitrary direction irrespective of the posture of the inverted vehicle; and a position determining unit that determines a position of the inverted vehicle, wherein when a distance between the position of the inverted vehicle obtained by the position determining unit and a reference position is greater than or equal to a threshold, the control unit suppresses only the control to forcibly move the inverted vehicle in a direction from the reference position to the position of the inverted vehicle when the control unit controls the inverted vehicle so that the inverted vehicle is forcibly moved in an arbitrary direction irrespective of the posture of the inverted vehicle.

6. The balance training device according to claim 1, wherein the inverted vehicle includes two wheels.

7. The inverted vehicle according to claim 5, wherein the inverted vehicle includes two wheels.

\* \* \* \* \*